United States Patent [19]

Hoogstraat

[11] 4,346,583

[45] Aug. 31, 1982

[54] METHOD AND APPARATUS FOR DETERMINING THE HYDROGEN CONTENT OF A GAS

[76] Inventor: Herman M. Hoogstraat, 10 Passeweg 8, 8084 AN'tHarde, Netherlands

[21] Appl. No.: 45,879

[22] Filed: Jun. 6, 1979

[30] Foreign Application Priority Data

Jun. 12, 1978 [NL] Netherlands .......................... 7806340

[51] Int. Cl.³ .............................................. G01N 31/00
[52] U.S. Cl. ........................................ 73/19; 128/719
[58] Field of Search ................... 73/19, 23, 23.1, 27 R, 73/421.5 R; 128/718, 719; 422/84; 340/632, 633, 634

[56] References Cited

U.S. PATENT DOCUMENTS

| | | | |
|---|---|---|---|
| 3,714,421 | 1/1973 | Josias et al. | 73/23.1 |
| 3,824,168 | 7/1974 | Oswin et al. | 128/719 |
| 3,854,320 | 12/1974 | Burroughs et al. | 422/84 |
| 3,895,630 | 7/1975 | Bachman | 422/84 |

*Primary Examiner*—Stephen A. Kreitman
*Attorney, Agent, or Firm*—McGlew and Tuttle

[57] ABSTRACT

Determining the hydrogen content of the expiratory air of a person using a sample holder and a hydrogen detector. Expiratory air is passed through the sample holder in order to obtain an expiratory air sample. A pressurized gas is then introduced into the sample holder and directs the expiratory air through the hydrogen detector at a fixed flow rate as determined by the pressure of the pressurized gas.

3 Claims, 2 Drawing Figures

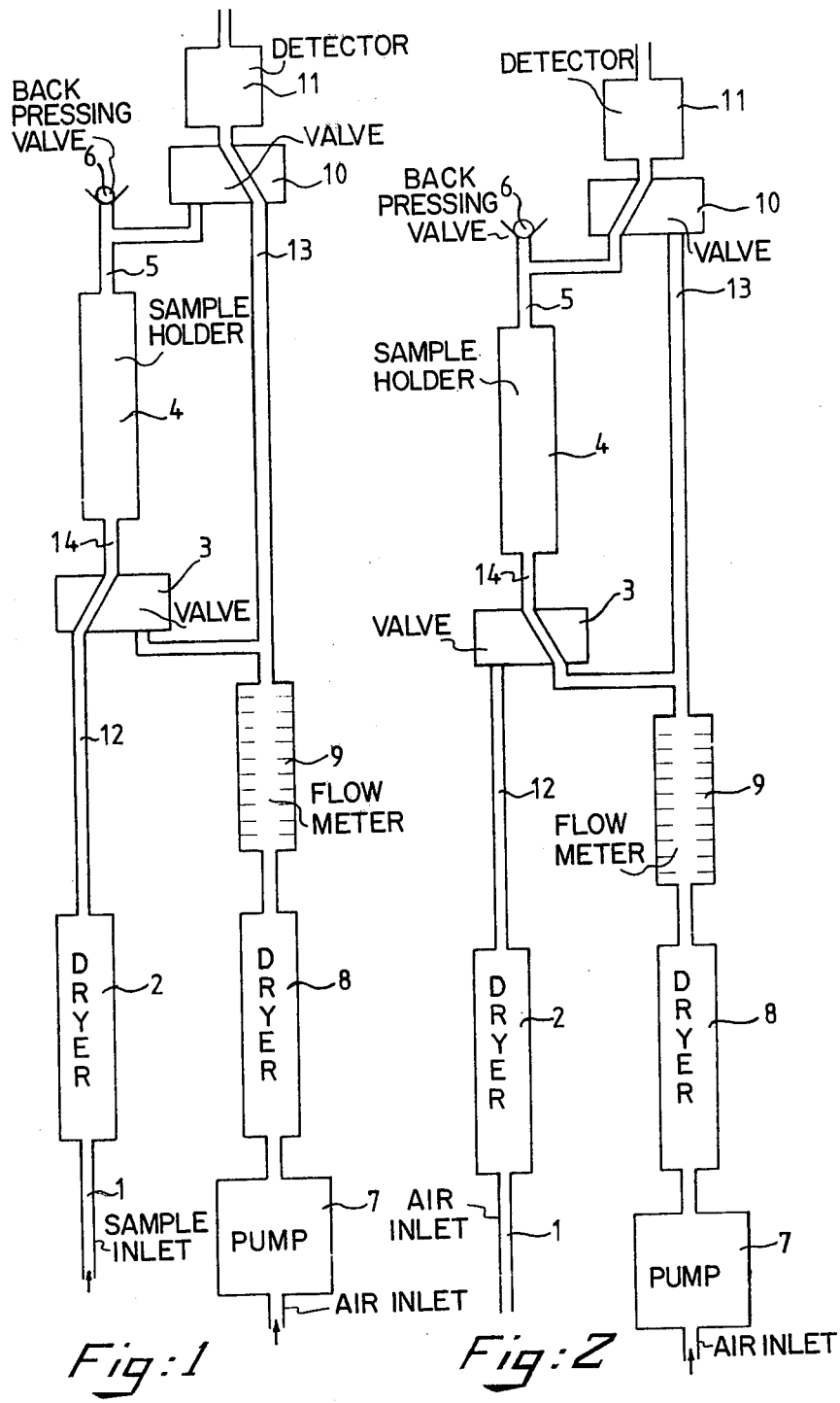
Fig:1    Fig:2

METHOD AND APPARATUS FOR DETERMINING THE HYDROGEN CONTENT OF A GAS

BACKGROUND OF THE INVENTION

The invention relates to a method for determining the hydrogen content of a gas and more specifically the hydrogen content of a person's expiratory air, and also to an apparatus for putting this method into practice.

As is known the hydrogen content of a person's expiratory air corresponds with the hydrogen production in the intestinal lumen. It therefore is possible to detect an abnormal breakdown and/or malabsorbtion of carbohydrates by sampling the expiratory air regularly during a certain period and measuring the hydrogen content thereof. Thus the hydrogen content of the samples is determined. Until now, the method used to determine the hydrogen content in expiratory air is very cumbersome, requires expensive devices, such as a gaschromatograph which must be operated by qualified people, and takes several hours to obtain the final results of the measurements.

SUMMARY OF THE INVENTION

The object of the invention is to provide a method for determining the hydrogen content of a gas sample, such as a person's expiratory air, directly after sampling.

According to the method of the present invention the hydrogen content of a gas is determined by leading or passing the gas of which the hydrogen content is to be determined through a sample-holder, obtaining a sample of the gas to be measured by closing the outlet and inlet of the sample-holder and, finally, determining the hydrogen-content by connecting the outlet of the sample-holder with a detector and introducing air or another gas at a fixed rate at a predetermined overpressure into the inlet of the sample-holder, so as to drive the contents of the sample-holder i.e. the gas-sample, through the detector at the fixed rate. In this manner, the measurement of the hydrogen content is carried out directly after the sampling, in situ, and the hydrogen content is determined within minutes. Data become quickly available because a number of time consuming actions, such as transporting sample-holders and placing sample-holders into a gaschromatograph are eliminated.

According to a preferred method of the present invention, the hydrogen content of a gas is determined by passing or leading air or another gas at a fixed rate and during a predetermined minimum time-period through a sample-holder and a detector, leading through the sample-holder the gas of which the hydrogen content is to be determined and at the same time leading through the detector air or another gas at a fixed rate, obtaining a sample of the gas to be measured by closing the outlet and inlet of the sample-holder and, finally, determining the hydrogen content by connecting the outlet of the sample-holder with a detector an introducing air or another gas at a fixed rate at a predetermined overpressure into the inlet of the sample-holder, so as to drive the contents of the sample-holder, i.e. the gas-sample, through the detector at the fixed rate. In this manner the temperature of the detector remains constant so that the measurements will be reproducible.

According to the invention, an apparatus for determining the hydrogen-content of a person's expiratory air comprises a sample-holder, a pump, valves and a detector to measure the hydrogen content in a gas which detector is sensitive for gas and smoke and determines the hydrogen content by means of diffusion. An apparatus according to the invention is comparatively cheaper than an expensive gaschromatograph and an inexpensive detector, may be used.

The invention may be performed in various ways and one specific embodiment will now be described by way of example with reference to the accompanying drawings. While a specific embodiment of the invention has been shown and described in detail to illustrate the application of the principles of the invention, it will be understood that the invention may be embodied otherwise without departing from such principles.

It is an object of the invention to provide a method of determining the hydrogen content of the expiratory air of a person using a sample holder and a hydrogen detector which comprises the steps of passing expiratory air through the sample holder to obtain an expiratory air sample, and introducing a pressurized gas into the sample holder to direct the expiratory air and through the hydrogen detector at a fixed flow rate as determined by the pressure of the pressurized gas. It is a further object of the invention to provide an apparatus for determining the hydrogen content of the expiratory air of a person which comprises a hydrogen detector, a sample holder including a housing having an inlet and an outlet, a first valve member connected to said inlet, a second valve member connected to the outlet and the hydrogen detector, tube means for passing expiratory air into the sample holder and the first valve member, conduit means connected to the first valve member and the second valve member, pump means for passing a gas under pressure into the conduit means, the first valve member being operative for selectively closing the inlet and opening the inlet alternately to the tube means and the conduit means, the second valve member being operative for selectively closing the outlet and alternately opening the outlet and the conduit means for passing a fluid under pressure through the hydrogen detector at a fixed flow rate.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

FIGS. 1 and 2 are schematic representations of an apparatus arrangement according to the invention.

DETAILED DESCRIPTION

Both FIGS. 1 and 2 illustrate an apparatus for determining the hydrogen content of a gas. The gas of which the hydrogen content has to be determined, is passed (FIG. 1) before sampling via an inlet 1, a first dryer 2, a tube 12, a valve 3, a sample-holder 4 with an inlet 14 and an outlet 5, through a back pressing valve 6 into the air. At the same time, by means of a pump 7, air is lead through a second dryer 8, a flowmeter 9, a second tube 13, a second valve 10 and a detector 11.

FIG. 2 shows in outline the same apparatus as shown in FIG. 1, however the valves 3 and 10 are aligned so that the pump 7 is interconnected with the detector 11 via the sample-holder 4 and no longer via the tube 13.

Hereinafter the method for determining the hydrogen content of a gas will be described more in detail.

With the valves 3 and 10 in the position as shown in FIG. 2 air is pumped through the sample-holder 4 for at least several minutes. Then, the valves 3 and 10 are brought into the position, as shown in FIG. 1, and a patient is asked to exhale deeply into the inlet 1 which may be a flexible, disposable tube attached to the unit. The expiratory air thus admitted is conducted through the sample-holder 4 and the back-pressing valve 6. Then, the valves 3 and 10 are brought back into the alignment position as shown in FIG. 2 and slowly, by means of the pump 7, the expiratory air sample is driven out of the sample-holder 4 and through the measuring cell or detector 11. The back-pressing valve 6 is adjusted such that no gas will escape by this valve 6 when the sample-holder 4 is connected to the detector 11.

A detector preferably used is a semiconductor, sensitive to gas and smoke, such as MXE, type CL 10. This kind of detector is sensitive to several gases, but, hydrogen having the highest velocity of diffusion, it will be from all gases the first to penetrate into the detector. So when the composition of the gas streaming along the detector is suddenly changed, the detector will emit a signal directly proportional to the difference in hydrogen content of the gas before (i.e. air) and after (i.e. expiratory air) the change in composition.

The actual detection of the hydrogen content does not commence until 10 seconds after the introduction of the gas-sample. By means of an electronic circuit, the signal from the detector, being proportional to the hydrogen content, is registered and shown on a gauge and then retained for approximately 5 minutes. During this time the measuring system is scavenged automatically with air from the atmosphere and the valves 3 and 10 are blocked in a position as shown in FIG. 2. When the 5 minute period is over, the gauge indicator resumes zero position, the valves 3 and 10 are no longer blocked, and the unit is ready for the next run.

Thus, the starting condition of each measurement will be comparable. Because the predetermined overpressure is constant, the gas stream flow through the detector remains constant and the detector is always kept under the same working conditions (temperature, humidity etc.). The rate or velocity of the gas stream is in the preferred embodiment less than 10 liter per hour (3 cm$^3$/sec.).

While a specific embodiment of the invention has been shown and described in detail to illustrate the application of the principles of the invention, it will be understood that the invention may be embodied otherwise without departing from such principles.

What is claimed is:

1. A method for determining the hydrogen content of a gas and more specifically the hydrogen content of a person's expiratory air comprising the following steps: leading the gas of which the hydrogen content is to be determined through a sample-holder, sampling the gas to be measured by closing the outlet and inlet of the sample-holder and, finally, determining the hydrogen content by connecting the outlet of the sample-holder with a detector and introducing air or another gas at a fixed rate at a predetermined overpressure into the inlet of the sample-holder, so as to drive the contents of the sample-holder i.e. the gas-sample through the detector at a fixed rate.

2. An apparatus for determining the hydrogen content of the expiratory air of a person which comprises a hydrogen detector, a sample holder including a housing having an inlet and an outlet, a first valve member connected to said inlet, a second valve member connected to said outlet and said hydrogen detector, tube means for passing expiratory air into said sample holder and said first valve member, conduit means connected to said first valve member and said second valve member, pump means for passing a gas under pressure into said conduit means, said first valve member being operative for selectively closing said inlet and opening said inlet alternately to said tube means and said conduit means, said second valve member being operative for selectively closing said outlet and alternately opening said outlet and said conduit means for passing a fluid under pressure to said hydrogen detector at a fixed flow rate.

3. A method of determining the hydrogen content of the expiratory air of a person using a sample holder and a hydrogen detector which comprises the steps of directing a stream of a pressurized gas through the hydrogen detector at the fixed flow rate, detecting the presence of hydrogen in the pressurized gas, passing expiratory air through the sample holder to obtain an expiratory air sample, and introducing the pressurized gas into the sample holder to direct a stream of the expiratory air through the hydrogen detector at a fixed flow rate as determined by the pressure of the pressurized gas and determining the hydrogen content in said expiratory air by generating a signal proportional to the difference of hydrogen in said stream of the pressurized gas and said stream of said expiratory air.

* * * * *

UNITED STATES PATENT AND TRADEMARK OFFICE
CERTIFICATE OF CORRECTION

PATENT NO. : 4,346,583
DATED : August 31, 1982
INVENTOR(S) : Herman M. Hoogstraat It is certified that error appears in the above-identified patent and that said Letters Patent is hereby corrected as shown below:

In Fig. 2, the label "AIR INLET" on line 1 should read
-- INLET --.

Signed and Sealed this

Seventh Day of December 1982

[SEAL]

Attest:

GERALD J. MOSSINGHOFF

Attesting Officer    Commissioner of Patents and Trademarks